US008841229B2

(12) United States Patent
Terorde et al.

(10) Patent No.: US 8,841,229 B2
(45) Date of Patent: Sep. 23, 2014

(54) PROCESS FOR THE PREPARATION OF FISCHER-TROPSCHE CATALYSTS AND THEIR USE

(75) Inventors: Robert Johan Andreas Maria Terorde, Maam (NL); Luuk Laurentius Kramer, Karmerik (NL)

(73) Assignee: Sasol Technology (Proprietary) Limited, Johannesburg (ZA)

( * ) Notice: Subject to any disclaimer, the term of this patent is extended or adjusted under 35 U.S.C. 154(b) by 179 days.

(21) Appl. No.: 13/201,715

(22) PCT Filed: Feb. 23, 2010

(86) PCT No.: PCT/IB2010/050783
§ 371 (c)(1),
(2), (4) Date: Aug. 16, 2011

(87) PCT Pub. No.: WO2010/097754
PCT Pub. Date: Sep. 2, 2010

(65) Prior Publication Data
US 2011/0301024 A1 Dec. 8, 2011

Related U.S. Application Data

(60) Provisional application No. 61/155,781, filed on Feb. 26, 2009.

(30) Foreign Application Priority Data

Feb. 26, 2009 (ZA) .................................. 2009/01400

(51) Int. Cl.
*B01J 21/00* (2006.01)
*B01J 23/00* (2006.01)
*B01J 23/40* (2006.01)
*B01J 23/42* (2006.01)
*C07C 27/00* (2006.01)
*C10G 45/00* (2006.01)
*C07C 51/36* (2006.01)
*B01J 37/02* (2006.01)
*C10G 2/00* (2006.01)
*B01J 23/89* (2006.01)
*C10G 3/00* (2006.01)
*B01J 23/889* (2006.01)

(52) U.S. Cl.
CPC ............... *C10G 3/45* (2013.01); *B10J 37/0205* (2013.01); *B10J 35/006* (2013.01); *C10G 45/00* (2013.01); *B01J 2523/00* (2013.01); *C07C 51/36* (2013.01); *B01J 37/024* (2013.01); *C10G 2/33* (2013.01); *B01J 23/8913* (2013.01); *C10G 3/56* (2013.01); *B01J 23/002* (2013.01); *C10G 2/332* (2013.01); *B01J 23/8896* (2013.01); *B01J 37/0203* (2013.01); *C10G 3/50* (2013.01); *C01G 2300/70* (2013.01); *C10G 3/48* (2013.01)
USPC ........... 502/259; 502/326; 502/327; 502/335; 502/337; 518/715

(58) Field of Classification Search
CPC .......... B01J 23/75; B01J 23/755; B01J 23/76; B01J 37/0201; B01J 37/0203; B01J 37/0205; B01J 37/0213; B01J 37/0236; B01J 37/024; B01J 37/088; B01J 37/16; B01J 37/18; B01J 21/00; C07C 2523/75; C07C 2523/755; C10G 2/332
USPC ........... 502/259, 260, 327, 335, 337; 518/715
See application file for complete search history.

(56) References Cited

U.S. PATENT DOCUMENTS

| 4,052,335 | A | * | 10/1977 | Michalczyk et al. ......... 502/185 |
| 5,856,260 | A | | 1/1999 | Mauldin |
| 5,856,365 | A | * | 1/1999 | Zennaro et al. ............... 518/715 |
| 5,945,459 | A | | 8/1999 | Mauldin |

(Continued)

FOREIGN PATENT DOCUMENTS

| EP | 0736326 B1 | 8/2001 |
| WO | WO0176734 A1 | 10/2001 |

(Continued)

OTHER PUBLICATIONS

Matsuzaki, "Hydrogenation of carbon monoxide over highly dispersed cobalt catalysts derived from cobalt (II) acetate", "Catalysis Today XP-002545697", 1996, pp. 251-259, vol. 28, Published in: US.
Kraum, M. et al., "Fischer-Tropsch Synthesis: The Influence of Various Cobalt Compounds Applied in the Preparation of Supported Cobalt Cata", Oct. 4, 1999, pp. 189-200, vol. 186, No. 1-2, Publisher: Applied Catalysts A: General, Elsevier Science, Amsterdam, NL XP004271933.

(Continued)

*Primary Examiner* — Cam N. Nguyen
(74) *Attorney, Agent, or Firm* — Fellers, Snider, Blankenship, Bailey & Tippens, P.C.

(57) ABSTRACT

A process for preparing a catalyst precursor includes, in a first preparation step, impregnating a particulate catalyst support with an organic metal compound in a carrier liquid. The metal of the organic metal compound is an active catalyst component. An impregnated intermediate is formed, and is calcined to obtain a calcined intermediate. Thereafter, in a second preparation step, the calcined intermediate from the first preparation step is impregnated with an inorganic metal salt in a carrier liquid. The metal of the inorganic metal salt is an active catalyst component. An impregnated support is obtained, and is calcined, to obtain the catalyst precursor. The metal is in particular cobalt. The precursor is reduced, in particular with hydrogen, to obtain the active catalyst. Also claimed is a process for the hydrogenation of CO, as well as a process for the hydrogenation of an organic compound using the so-prepared catalyst.

20 Claims, No Drawings

(56) References Cited

U.S. PATENT DOCUMENTS

| | | | |
|---|---|---|---|
| 6,130,184 A * | 10/2000 | Geerlings et al. | 502/350 |
| 6,482,766 B1 * | 11/2002 | Chaumette et al. | 502/242 |
| 6,822,008 B2 | 11/2004 | Srinivasan et al. | |
| 7,427,581 B2 * | 9/2008 | Khare | 502/406 |
| 7,560,412 B2 * | 7/2009 | Osbourne et al. | 502/327 |
| 7,598,203 B2 * | 10/2009 | Kagami et al. | 502/309 |
| 7,605,107 B2 * | 10/2009 | Soled et al. | 502/216 |
| 7,732,370 B2 * | 6/2010 | Casci et al. | 502/329 |
| 7,851,404 B2 * | 12/2010 | Lok | 502/326 |
| 8,003,564 B2 * | 8/2011 | Dogterom et al. | 502/325 |
| 2003/0111391 A1 | 6/2003 | Bhan | |
| 2004/0048937 A1 | 3/2004 | Srinivasan et al. | |
| 2005/0026776 A1 | 2/2005 | Yamada et al. | |
| 2008/0255257 A1 * | 10/2008 | Kuipers et al. | 518/715 |
| 2009/0187036 A1 * | 7/2009 | Hagemeyer | 556/140 |
| 2009/0286678 A1 * | 11/2009 | Hagemeyer | 502/304 |
| 2010/0048742 A1 * | 2/2010 | Ellis et al. | 518/717 |
| 2010/0137642 A1 * | 6/2010 | King et al. | 564/470 |
| 2010/0168259 A1 * | 7/2010 | Xiao et al. | 518/719 |
| 2010/0261601 A1 * | 10/2010 | Robota et al. | 502/241 |

FOREIGN PATENT DOCUMENTS

| | | | |
|---|---|---|---|
| WO | WO02089978 A1 | 11/2002 | |
| WO | 2004028687 A1 | 4/2004 | |
| WO | W02009127990 A1 | 10/2009 | |

OTHER PUBLICATIONS

Matsuzaki, T., et al., "Effect of Transition Metals on Oxygenates Formation From Syngas Over CO/Si02", Nov. 15, 1993, pp. 159-184, vol. 105, No. 2, Publisher: Applied Catalysts A: General, XP002616992.

Sun S. et al., "Active Co/Si02 Catalysts Prepared From Mixing Precursors for Slurry Phasefischer-Tropsch Synthesis", 1999, pp. 343-344, vol. 28, No. 4, Publisher: Chemistry Letters, XP9142959; ISSN: 1348-0715, DOI: 10.1246/cl.1999.343.

Van De Loosdrecht, J., et al., "Preparation and Properties of Supported Cobalt Catalyts for Fischer-Tropsch Synthesis", Mar. 13, 1997, pp. 365-376, vol. 150, No. 2, Publisher: Applied Catalysts A: General, Elsevier Science, Amsterdam, NL XP004338059 ISSN: 0926-86OX.

European Patent Office PCT International Search Report, International Application PCT/IB2010/050783, mailed Apr. 7, 2011.

European Patent Office PCT Written Opinion, International Application PCT/IB2010/050783, mailed Apr. 7, 2011.

PCT/1B2010/050783, International Preliminary Report on Patentability, Isssued: Aug. 30, 2011.

* cited by examiner

US 8,841,229 B2

PROCESS FOR THE PREPARATION OF FISCHER-TROPSCHE CATALYSTS AND THEIR USE

FIELD OF THE INVENTION

THIS INVENTION relates to catalysts. It relates in particular to a process for preparing a catalyst precursor, and to a process for preparing a catalyst, which catalyst can be used, for instance, in hydrocarbon synthesis (including Fischer-Tropsch (FT)) and hydrogenation reactions.

BACKGROUND ART

Preparation of Catalyst Precursors by Metal Impregnation onto Catalyst supports using various impregnation techniques, is well known to those skilled in the art. The impregnated supports so obtained are then usually subjected to drying and calcination to provide catalyst precursors, and the precursors are then subjected to reduction to produce, finally, a catalyst.

In particular, the Applicants are aware that, as described in EP 0736326 B1, cobalt impregnated alumina based Fischer-Tropsch synthesis catalysts can, for example, be synthesized by means of aqueous slurry phase impregnation of a cobalt salt, for example cobalt nitrate hexahydrate, onto an alumina support, coupled with drying of the impregnated support, followed by direct fluidized bed calcination of the resultant impregnated support, to obtain a catalyst precursor, and then reducing the precursor to obtain the Fischer-Tropsch synthesis catalysts. The catalysts contain cobalt dispersed on the support. Sufficiently high cobalt loadings to provide a desired high degree of catalyst activity can readily be obtained by means of the cobalt salt impregnation, by repeating, if necessary, the cobalt salt impregnation step.

It has been reported that the use of organic metal compounds or organic additives during the impregnation could assist in increasing the catalyst activity of supported metal catalysts. For example, U.S. Pat. No. 5,856,260 teaches that using mixtures of polyols and metal salts during impregnation results in improved catalyst performance.

Van de Loosdrecht et. al. (Applied Catalysis A: General, Volume 150, Number 2, 13 Mar. 1997, pp 365-376(12)) reported that the preparation of low loading cobalt catalysts (2.5% Co) by impregnation using Co-EDTA (ethylenediaminetetraacetic acid) or ammonium cobalt citrate resulted initially in the formation of very small cobalt oxide particles. These small oxide particles reacted during thermal treatment in a reducing gas flow with the alumina support to form cobalt aluminate, which was inactive in Fischer-Tropsch synthesis. Higher loading catalysts (5% Co) prepared by a 2 step impregnation process using ammonium cobalt citrate in both steps resulted in a larger cobalt oxide particle size and higher reducibility, culminating in a reasonable activity, but still lower compared to a reference catalyst prepared from impregnation with cobalt nitrate only and having similar cobalt loading.

The use of organic impregnation compounds tends to result in low metal loadings due to limited solubility and high viscosity of the impregnation solution. For many catalytic reactions, the low loadings of metal do not provide sufficiently high activity, due to, amongst other reasons, the low reducibility of such catalysts.

Kraum and Baern (Applied Catalysis A: General 186 (1999)189-200) describe studies of the performance of titania supported catalysts containing 12% cobalt, prepared by multiple impregnations with various organic cobalt compounds, including cobalt(III) acetyl acetonate, cobalt acetate, cobalt oxalate and cobalt-EDTA. The multiple impregnations were performed for each particular catalyst using only a single organic cobalt compound. In this study, sufficiently high metal loadings were only achieved by performing multiple impregnation cycles, thereby compensating for the low solubility of the organic cobalt compounds. However, having to use multiple impregnation cycles for the preparation of a catalyst can be economically unattractive.

U.S. Pat. No. 6,822,008B2 teaches the use of two different metal precursors loaded separately on to a suitable support, in such manner that the first loaded portion of metal is more easily reduced, than the second loaded portion of metal. For example, cobalt nitrate hexahydrate is loaded first, whereafter cobalt acetate is loaded on to the support. The second cobalt precursor can thus be an organic cobalt salt such as cobalt acetate. However, U.S. Pat. No. 6,822,008B2 does not demonstrate an increase in cobalt dispersion or an increase in FT synthesis activity.

It is thus an object of the present invention to provide a catalyst precursor and/or a catalyst with which some of the disadvantages described above are overcome or at least reduced.

DISCLOSURE OF THE INVENTION

Thus, according to a first aspect of the invention, there is provided a process for preparing a catalyst precursor, which process includes in a first preparation step, impregnating a particulate catalyst support with an organic metal compound in a carrier liquid, wherein the metal of the organic metal compound is an active catalyst component, to form an impregnated intermediate, and calcining the impregnated intermediate, to obtain a calcined intermediate; and thereafter, in a second preparation step, impregnating the calcined intermediate from the first preparation step, with an inorganic metal salt in a carrier liquid, wherein the metal of the inorganic salt is an active catalyst component, to obtain an impregnated support, and calcining the impregnated support, to obtain the catalyst precursor.

In a preferred embodiment of the invention, the impregnated intermediate of the first preparation step is at least partially dried prior to the calcination thereof. Preferably, the impregnated support of the second preparation step is also at least partially dried prior to the calcination thereof. It will be appreciated that the partial drying will usually take place where the impregnation is slurry phase impregnation.

By "active catalyst component" is meant that the metal of the organic metal compound and that of the inorganic metal compound are such that they actively catalyse chemical reactions wherein an eventual catalyst obtained from the catalyst precursor, is used as a catalyst Thus, impregnation with compounds which do not eventually actively catalyse said chemical reactions, is excluded. Examples of such excluded compounds are silica compounds which, if used, would serve to modify the support, rather than actively catalyse the chemical reaction wherein the eventual catalyst is used as a catalyst.

The invention is thus characterized thereby that the impregnation is strictly carried out using the sequence of impregnation first with the organic metal compound and thereafter, after the calcining of the impregnated intermediate, impregnation with the inorganic metal salt. Preferably, none of the inorganic metal salt used in the second preparation step is present during the first impregnation step. Preferably, none of the organic metal compound of the first preparation step is present during the second preparation step.

The present invention thus provides a process for preparing a metal, preferably cobalt, based catalyst precursor from which is obtained a catalyst which may have increased activity. Surprisingly, it was found that after having effected an initial or first preparation step involving an impregnation using an organic metal compound such as ammonium cobalt citrate, if in a next or second preparation step cobalt is impregnated using an inorganic metal salt such as cobalt nitrate, a high metal, e.g. cobalt, dispersion is usually obtained and at the same time, a high loading of metal, e.g. cobalt, may be achieved, usually with an increased catalyst activity compared to the standard manner of preparing such catalysts using only inorganic cobalt salts in two sequential impregnation steps. This increased catalyst activity is achieved at a metal, e.g. cobalt, loading which is similar to, or even lower than, catalysts prepared using the standard manner of impregnation with inorganic metal salts in two sequential impregnation steps. Since the intermediate obtained after the first preparation or impregnation step only contains an organic metal compound and not the usual nitrate, the exothermic decomposition of this compound can be very well controlled.

It is believed that the increased catalyst activity may be due to the fact that after the first impregnation with the organic metal precursor, a high metal, e.g. cobalt, dispersion is usually obtained with a limited reducibility, while after the second impregnation with the inorganic metal salt, the high dispersion is surprisingly maintained, but the reducibility and metal loading are increased, resulting in a catalyst with better dispersion and similar loading and reducibility compared to catalysts prepared using the standard manner of impregnation with inorganic cobalt salts in two sequential impregnation steps. It is thus believed that the higher metal, e.g. cobalt, dispersion while having the correct metal loading and reducibility, has resulted in an increased catalyst activity.

In this specification, the term "organic metal compound" means a compound wherein at least one metal atom is associated with at least one organic group by means of a bond, for instance, by means of a covalent bond, a metal-to-ligand coordination or an ionic interaction. Preferably, the metal atom is associated to at least one non-carbon atom of the at least one organic group, in particular to an oxygen atom of the organic group. The organic metal compound may also include one or more inorganic groups bound to the metal. Preferably, the one or more inorganic groups are cationic groups.

In this specification, the term "inorganic metal salt" means a salt wherein at least one metal atom is only associated with one or more inorganic groups, which association is by means of a bond, for instance, by means of a covalent bond, a metal-to-ligand coordination or an ionic interaction.

The process may include, in the first preparation step, repeating, at least once, the impregnation with the organic metal compound. Preferably, also the at least partial drying of the impregnated intermediate is then repeated, that is, when at least partial drying is carried out. Preferably, also the calcination of the impregnated intermediate is then also repeated. In this fashion, a higher metal loading in the calcined intermediate, is obtained.

Likewise, the process may include, in the second preparation step, repeating, at least once, the impregnation with the inorganic metal salt. Preferably, also the at least partial drying of the impregnated support is then repeated, that is, when at least partial drying is carried out. Preferably, also the calcination of the impregnated support is then repeated. In this fashion, a higher metal loading in the catalyst precursor, is obtained.

Thus, in one embodiment of the invention, the first preparation step may comprise a first impregnation with the organic metal compound, at least partial drying (optional) and calcination, as hereinbefore described, followed by a second impregnation with the organic metal compound, at least partial drying (optional), and calcination, as hereinbefore described; the second preparation step may then comprise a single impregnation with the inorganic metal salt, at least partial drying (optional), and calcination, as hereinbefore described.

However, in another embodiment of the invention, the first preparation stage may comprise a single impregnation with the organic metal compound, at least partial drying (optional) and calcination, as hereinbefore described; the second preparation step may then comprise a first impregnation with the inorganic metal salt, at least partial drying (optional), and calcination, as hereinbefore described, followed by a second impregnation with the inorganic metal salt, at least partial drying (optional), and calcination, as hereinbefore described.

The metal of the organic metal compound and the metal of the inorganic metal salt may be the same or different metals. Preferably, however, they are the same metal. Suitable metals for the purpose of the present invention are high value metals, such as precious metals. Most suitable metals in accordance with the present invention are cobalt and nickel.

In a first embodiment of the invention, the catalyst precursor may be a hydrocarbon synthesis catalyst precursor. Preferably, it may then be a Fischer-Tropsch synthesis catalyst precursor. More preferably, it may then be a slurry phase Fischer-Tropsch synthesis catalyst precursor. The metal of the organic metal compound may be cobalt. Preferably, the metal of the inorganic metal salt is then also cobalt, which is thus the active component of the eventual catalyst. The catalyst precursor is then a cobalt-based Fischer-Tropsch synthesis catalyst precursor.

It was found that when a cobalt-based Fischer-Tropsch synthesis catalyst precursor as set out above is converted to a Fischer-Tropsch synthesis catalyst by means of reduction, the catalyst has a high and stable Fischer-Tropsch activity. Furthermore, it was surprisingly found that by using the two-step preparation process as hereinbefore defined, not only is a desired high cobalt loading obtained, but a high degree of cobalt (metal and/or oxide) dispersion is also obtained, resulting in a catalyst with improved Fischer-Tropsch synthesis activity.

The inorganic cobalt salt of the second preparation step may, at least in principle, be any inorganic cobalt salt; however, cobalt nitrate, and in particular, $Co(NO_3)_2 \cdot 6H_2O$, is preferred.

Preferably the inorganic cobalt salt is at least partly dissolved in the carrier liquid. The carrier liquid may thus be any suitable liquid solvent. Preferably, however, it is water.

Likewise, the organic cobalt compound of the first preparation step is preferably at least partly dissolved in the carrier liquid. The carrier liquid may be any suitable liquid solvent. Preferably, however, it is water.

The organic cobalt compound may be that obtained by reacting a cobalt compound such as cobalt hydroxide, with an organic acid, optionally in the presence of at least one counterion source.

The cobalt compound preferably is a cobalt basic compound.

The counterion source, when present, is preferably an inorganic source, and preferably it is a source of one or more cations. In one embodiment of the invention, the counterion source may be ammonia.

The organic cobalt compound can be formed in situ. Thus, the cobalt compound, e.g. cobalt hydroxide, can be dissolved in a solution of the organic acid in water.

The organic acid may be a carboxylic acid such as citric acid ($C_6H_8O_7$), succinic acid ($C_4H_6O_4$), oxalic acid ($C_2H_2O_4$), acetic acid ($C_2H_4O_2$), gluconic acid ($C_6H_{12}O_7$) or EDTA, i.e. ethylenediaminetetraacetic acid. Preferably, the organic acid is citric acid.

In the organic cobalt compound solution, the molar ratio of cobalt to organic acid can vary widely, e.g. from 0.1:1 to 10:1. However, it is expected that the molar ratio of cobalt to organic acid will normally be in the range of 0.5:1 to 2:1, typically about 1:1.

In preferred embodiments of the invention, the organic cobalt compound of the first preparation step may be cobalt ammonium citrate or cobalt ammonium EDTA.

Instead, the organic cobalt compound of the first preparation step may be that obtained by reaction of a cobalt compound with acetylacetone ($C_5H_8O_2$).

The catalyst support may be a particulate porous support.

The catalyst support may comprise a catalyst support basis and optionally one or more modifying components. The catalyst support basis may be selected from the group consisting of alumina in the form of one or more aluminium oxides; silica ($SiO_2$); titania ($TiO_2$); magnesia (MgO); and zinc oxide (ZnO); and mixtures thereof. Preferably the support basis is selected from the group consisting of alumina in the form of one or more aluminium oxides; titania ($TiO_2$) and silica ($SiO_2$). Typically, the support basis is alumina in the form of one or more aluminium oxides. The one or more aluminium oxides may be selected from the group including (preferably consisting of) gamma alumina, delta alumina, theta alumina and a mixture of two or more thereof. Preferably the group includes, or, preferably, consists of gamma alumina, delta alumina and a mixture of gamma alumina and delta alumina. The aluminium oxide catalyst support may be that obtainable under the trademark Puralox, preferably Puralox SCCa 2/150 from SASOL Germany GmbH. Puralox SCCa 2/150 (trademark) is a spray-dried aluminium oxide support consisting of a mixture of gamma and delta aluminium oxide.

The aluminium oxide is preferably a crystalline compound which can be described by the formula $Al_2O_3.xH_2O$ where $0<x<1$. The term aluminium oxide thus excludes $Al(OH)_3$, and AlO(OH), but includes compounds such as gamma, delta and theta alumina.

Preferably, the catalyst support includes one or more modifying components. This is particularly the case where the support basis is soluble in a neutral and/or an acidic aqueous solution, or where the support basis is susceptible to hydrothermal attack as described below.

The modifying component may comprise a component that results in one or more of the following:
(i) decreases the dissolution of the catalyst support in an aqueous environment,
(ii) suppresses the susceptibility of the catalyst support to hydrothermal attack (especially during Fischer-Tropsch synthesis);
(iii) increases the pore volume of the catalyst support;
(iv) increases the strength and/or attrition and/or abrasion resistance of the catalyst support.

In a preferred embodiment of the invention, the modifying component decreases the dissolution of the catalyst support in an aqueous environment, i.e. increases the inertness of the catalyst support towards dissolution in an aqueous environment and/or suppresses the susceptibility of the catalyst support to hydrothermal attack, especially during Fischer-Tropsch synthesis. Such an aqueous environment may include an aqueous acid solution and/or an aqueous neutral solution, especially such an environment encountered during an aqueous phase impregnation catalyst preparation step. Hydrothermal attack can cause the sintering of the catalyst support (for example aluminium oxide), dissolution of Al ions or break up of the catalyst particles during hydrocarbon synthesis, especially Fischer-Tropsch synthesis, due to exposure to high temperature and water.

The modifying component is typically present in an amount that results in a level thereof in the catalyst support of at least 0.06 atoms per square nanometer.

The modifying component may include or consist of Si, Zr, Co, Ti, Cu, Zn, Mn, Ba, Ni, Na, K, Ca, Sn, Cr, Fe, Li, Ti, Sr, Ga, Sb, V, Hf, Th, Ce, Ge, U, Nb, Ta, W, La and mixtures of two or more thereof.

The modifying component may, more particularly, be selected from the group consisting of Si; Zr; Cu; Zn; Mn; Ba; La; W; Ni and mixtures of one or more thereof. Preferably the modifying component is selected from the group consisting of Si and Zr. In a preferred embodiment of the invention the modifying component is Si.

When the modifying component is Si, the silicon level in the resultant catalyst support is at least 0.06 Si atoms per square nanometer of the catalyst support, preferably at least 0.13 Si atoms pre square nanometer of the catalyst support, and more preferably at least 0.26 Si atoms per square nanometer of the catalyst support.

Preferably, the upper level is 2.8 Si atoms/$nm^2$ of the catalyst support.

In one embodiment of the invention, a catalyst support in the form of one or more aluminium oxides or a silica modified aluminium oxide is preferred over supports such as silica and titania, since it is believed that these supports provide a much more attrition resistant catalyst. The catalyst support in the form of one or more aluminium oxides or a silica modified aluminium oxide may also include La. It is believed that La improves attrition resistance.

In another embodiment of the invention, a catalyst support in the form of one or more aluminium oxides or a silica modified aluminium oxide may include titanium, preferably in an amount, expressed as elemental titanium, of at least 500 ppm by weight, preferably from about 1000 ppm to about 2000 ppm by weight. It is believed that the addition of the titanium increases the activity of a catalyst formed from such a support, especially in the case of a cobalt FT catalyst, particularly when no noble metal promoters and preferably no Re or Te promoters are present in the catalyst. Preferably, the titanium is included in the internal structure of the support and, preferably, no titanium is present as a deposit on the support. It is believed that the presence of this titanium in the support also improves the attrition resistance of a catalyst which includes such a support.

In yet another embodiment of the invention, the catalyst support may be in the form of porous particles coated with carbon. In an alternative embodiment of the invention, the porous particles may, however, be free of such a carbon coating.

The catalyst support may be modified by introducing a modifying component precursor which includes a modifying component as described hereinabove onto and/or into a catalyst support material.

When present, the drying during the first and/or the second preparation steps, preferably during both preparation steps, may be carried out under conditions at which the inorganic cobalt salt and the organic cobalt compound will not readily decompose. Preferably, the drying during the first and/or second preparation steps is carried out at above 25° C. and preferably at sub-atmospheric pressure.

The impregnation and, preferably, also the drying during the first preparation step may be effected at above 25° C. and preferably at sub-atmospheric pressure. Sufficient of a mixture of the organic cobalt compound in the carrier liquid, which is preferably water as hereinbefore indicated, may be used so that the volume of the mixture exceeds the pore volume of the support, typically by about 30%. After contacting the support with the organic cobalt salt and carrier liquid mixture, the wet impregnated support may be slowly dried at sub-atmospheric pressure to a temperature in the range 40 to 120° C., typically about 100° C., with the final pressure typically being in the range 50 to 120 mbar(a), typically about 80 mbar(a).

In the first preparation step, the impregnation may be effected by slurry phase impregnation using a slurry made up of the support and a solution of the organic cobalt compound. Preferably, the solution of the organic cobalt compound is an aqueous solution.

During the second preparation step, the particulate calcined intermediate of the first preparation step, may be subjected to slurry phase impregnation with a slurry made up of the calcined intermediate particles and a solution of the inorganic cobalt salt in the carrier liquid, preferably water. Again, generally, the impregnation and, preferably, the drying may be effected at above 25° C. and/or at sub-atmospheric pressure.

The impregnation during the first and/or the second preparation step may instead be done by means of incipient wetness impregnation using sufficient impregnation solution to fill the pores of the support or the calcined intermediate particles. The impregnated support or intermediate may be dried at above 25° C. and if required at sub-atmospheric pressure. It might also be dried at atmospheric pressure under a flow of a gas such as air or nitrogen.

Sufficient organic cobalt compound and inorganic cobalt salt may be used so that the resultant catalyst precursor contains between 5 g Co/100 g support and 70 g Co/100 g support, preferably between 15 g Co/100 g support and 40 g Co/100 g support.

A dopant may also be introduced onto and/or into the catalyst support. When present, the dopant is preferably one that is capable of enhancing the reducibility of the active catalyst component. The dopant may be introduced as a dopant compound which is a compound of a metal selected from the group consisting of palladium (Pd), platinum (Pt), ruthenium (Ru), rhenium (Re) and a mixture of one or more thereof. Preferably, the dopant compound is an inorganic salt, and, preferably it is soluble in water. The mass proportion of the metal of the dopant (especially palladium or platinum) to the active component metal (especially cobalt) may be from 0.01:100 to 3:100.

The nitrogen content in the catalyst precursor may be less than 1 mass %, preferably less than 0.5 mass %.

Calcination is preferably carried out a temperature above 25° C. causing the impregnated cobalt compound and salt to decompose and/or to react with oxygen. Calcination is thus preferably carried out under oxidising conditions. For example, cobalt nitrate may be converted into a compound selected from $CoO$, $CoO(OH)$, $Co_3O_4$, $Co_2O_3$ or a mixture of one or more thereof.

The calcinations in the first and second preparation steps are typically effected in a fluidized bed, or in a rotary kiln. During the first preparation step, the at least partially dried impregnated support may be calcined using an air/nitrogen mixture. The oxygen content of this gas mixture may range from 0.01% to 20% (by volume), preferably from 0.5 to 20% (by volume). The calcination temperature may be above 95° C., preferably above 120° C., more preferably above 200° C., but preferably not above 400° C. Thus, the calcination temperature may be 250° C.-400° C., preferably from 280 to 330° C. The temperature is normally increased from ambient temperature, typically 25° C., to 250-400° C. at a rate of between 0.1 and 10° C./min, preferably between 0.5 and 3° C./min. The oxygen concentration can be kept constant during the calcination or it can be increased from a low oxygen concentration, e.i. i.e. 0.5-2 vol %, to a high concentration, (i.e. 10-20 vol %. The increase in oxygen concentration can be done during the temperature increase or during a hold time at the final temperature (250-400° C.). The GHSV during the calcination will normally be in the range of 100 to 3000 $h^{-1}$, typically about 2000 $h^{-1}$.

During the second preparation step, the at least partially dried impregnated intermediate may be calcined in air. The temperature during calcination may then be 200° C. to 350° C. The temperature is normally increased from ambient temperature, typically 25° C., to 200-350° C. at a rate of between 0.1 and 10° C./min, preferably between 0.5 and 3° C./min. The GHSV during the calcination will normally be in the range of 100 to 30001 $h^{-1}$, typically about 2000 $h^{-1}$. More particularly, the calcination conditions in the second preparation step may be selected such that, in the catalyst precursor, substantially all reducible cobalt is present in a calcined state.

The calcination during the first and/or the second preparation step may be carried out by using a heating rate and a space velocity that comply with the following criteria:
(i) when the heating rate is ≤1° C./min, the space velocity is at least 0.76 $m_n^3$/(kg $Co(NO_3)_2.6H_2O$)/h; and
(ii) when the heating rate is higher than 1° C./min, the space velocity satisfies the relation:

$$\log(\text{space velocity}) \geq \log 0.76 + \frac{\log 20 - \log 0.76}{2} \log(\text{heating rate})$$

As also indicated hereinbefore, the metal of the organic metal compound and that of the inorganic metal salt may be the same, and may be cobalt or nickel. Nickel is particularly suitable for preparing a hydrogenation catalyst precursor in accordance with the present invention.

In a second embodiment of the invention, the catalyst precursor may thus be a hydrogenation catalyst precursor suitable for the hydrogenation of organic compounds. More specifically, the catalyst precursor may then be an aromatics or an aldehyde hydrogenation catalyst precursor, or a hydrodechlorination catalyst precursor. For example, the catalyst precursor can then be an alcohol synthesis catalyst precursor.

When the hydrotreating catalyst precursor is cobalt-based, it can be formed in the same manner as the cobalt-based Fischer-Tropsch synthesis catalyst precursor hereinbefore described.

According to a second aspect of the invention, there is provided a process for preparing a catalyst, which includes reducing a catalyst precursor obtained by the process of the first aspect of the invention, thereby to obtain the catalyst.

When the catalyst precursor is a cobalt-based Fischer-Tropsch synthesis catalyst precursor as hereinbefore described, the catalyst will naturally be a Fischer-Tropsch synthesis catalyst.

When the catalyst precursor is a hydrogenation catalyst precursor as hereinbefore described, the catalyst will then naturally be a hydrogenation catalyst. The hydrogenation catalyst can then be used for hydrogenation of organic compounds such as oleochemicals (fatty materials: fats and oils, fatty acids and derivatives such as fatty nitriles, alcohols and aldehydes), petroleum fractions such as distillates, resins and the like, nitro compounds, olefins, diolefins, aromatic compounds, and the like.

More particularly, the hydrogenation catalyst can then be applied very suitably to the production of fine chemicals, wherein it is of importance that high selectivity is maintained. Examples of reactions that can be catalyzed by nickel-based catalysts prepared in accordance with the present invention are hydrogenation, hydro-dechlorination, and the like.

In hydro-dechlorination reactions, the hydrogenation catalyst of the invention makes it possible to control the amount of hydrogen and the hydrogen/HCl partial pressures in the system very carefully, thereby substantially improving the selectivity of the reaction.

The catalyst precursor may be activated by reduction by contacting the catalyst precursor with pure hydrogen or with a gaseous mixture containing hydrogen. The gaseous mixture may consist of hydrogen and one or more inert gases which are inert in respect of the active catalyst. The gaseous mixture preferably contains at least 90 volume % hydrogen. The reduction may be carried out at a temperature ranging from 250° C. to 550° C., preferably from about 300° C. to about 425° C., for a period ranging from 0.5 hour to about 24 hours and at a pressure ranging from ambient to about 40 atmospheres.

According to a third aspect of the present invention, there is provided a hydrocarbon synthesis process which comprises preparing a catalyst using the process of the second aspect of the invention; and contacting hydrogen with carbon monoxide at a temperature above 100° C. and a pressure of at least 10 bar with the catalyst so prepared, to produce hydrocarbons and, optionally, oxygenates of hydrocarbons.

The temperature may be from 180° C. to 250° C., more preferably from 210° C. to 240° C. The pressure more preferably may be from 10 bar to 40 bar.

Preferably, the hydrocarbon synthesis process is a Fischer-Tropsch process, more preferably a three phase Fischer-Tropsch process, still more preferably a slurry bed Fischer-Tropsch process for producing a wax product.

The hydrocarbon synthesis process may also include a hydroprocessing step for converting the hydrocarbons and, optionally, oxygenates to liquid fuels and/or chemicals.

The present invention extends also to products produced by the hydrocarbon synthesis process of the third aspect of the invention.

According to a fourth aspect of the present invention, there is provided a hydrogenation process which comprises preparing a catalyst using the process of the second aspect of the invention; and contacting hydrogen and an organic compound with the catalyst so prepared, to hydrogenate the organic compound.

The present invention extends also to products produced by the hydrogenation process of the fourth aspect of the invention.

EXAMPLES

The invention will now be described in more detail, with reference to the following non-limiting examples.

Example 1

Preparation of Comparative Catalyst A

A 30 g Co/0.075 g Pt/100 g (1.5 g Si/100 g Puralox SCCa 2/150) slurry phase Fischer-Tropsch synthesis ("FTS") catalyst was prepared on a particulate modified 1.5 g Si/100 g Puralox SCCa 2/150 (trademark) pre-shaped support using aqueous slurry phase impregnation and drying, followed by direct fluidised bed calcination in air.

This preparation was done by means of two impregnation and calcination steps, both using an inorganic cobalt compound.

In particular, the catalyst was prepared as follows:

43.70 g $Co(NO_3)_2.6H_2O$ were dissolved in 40 ml distilled water, and 0.024 g of $Pt(NH_3)_4.(NO_3)_2$ (dissolved in 10 ml distilled water) were added to this solution, where after 50.0 g of the 1.5 g Si/100 g Puralox SCCa 2/150 modified pre-shaped support were added to the solution. Aqueous slurry phase impregnation and vacuum drying were effected. This vacuum dried intermediate was directly subjected to a fluidized bed calcination step using a continuous air flow of 1.7 $dm^3{}_n$/min, while increasing the temperature from 25° C. to 250° C. at 1° C./min and keeping it at 250° C. for 6 hours. 50.0 g of this intermediate calcined material were subjected to the following $2^{nd}$ cobalt/platinum impregnation and calcination step: 23.51 g $Co(NO_3)_2.6H_2O$ were dissolved in 40 ml distilled water and 0.039 g of $Pt(NH_3)_4.(NO_3)_2$ (dissolved in 10 ml distilled water) were added to this solution, and 50.0 g of the ex $1^{st}$ cobalt/platinum impregnated and calcined intermediate were added. Aqueous slurry phase impregnation and vacuum drying were effected. This vacuum dried intermediate was directly subjected to a fluidized bed calcination step, according to the following procedure using a continuous air flow of 1.7 $dm^3{}_n$/min, while increasing the temperature from 25° C. to 250° C. at 1° C./min and keeping it at 250° C. for 6 hours.

In preparation for laboratory scale slurry phase continuous stirred tank reactor ('CSTR') Fischer-Tropsch synthesis (FTS) runs, this calcined material was reduced and wax coated in accordance with the following procedure: 10 g of the catalyst was reduced at 1 bar in pure $H_2$ (space velocity=2000 $ml_n$ $H_2$/g catalyst/h) whilst the temperature was increased from 25° C. to 425° C. at a rate of 1° C./min where after the temperature was kept constant at this temperature of 425° C. for 16 hours. The reduced catalyst was allowed to cool down to room temperature at which stage the hydrogen was replaced by argon, and the catalyst unloaded in molten Fischer-Tropsch wax under the protection of an argon blanket. This wax coated catalyst was then transferred to the slurry reactor.

Example 2

Preparation of Catalyst B in Accordance with the Invention

A 24 g Co/0.011 g Pd/0.061 g Pt/100 g (1.5 g Si/100 g Puralox SCCa 2/150) slurry phase Fischer-Tropsch synthesis ("FTS") catalyst was prepared on a particulate modified 1.5 g Si/100 g Puralox SCCa 2/150 (trademark) pre-shaped support using two sequential aqueous slurry phase preparation steps and drying, followed by direct fluidised bed calcination in an air/nitrogen mixture.

This preparation was done by means of two preparation steps: The first preparation step included a single impregnation step with an organic cobalt compound, while the second preparation step included a single impregnation step with an inorganic cobalt compound.

In particular, the catalyst was prepared as follows:

Preparation of Impregnation Solution 1

A cobalt ammonium citrate solution having a density of 1.3 g/ml and containing 125 g/l cobalt was prepared by dissolving cobalt hydroxide in a citric acid solution in a water/citric acid/cobalt hydroxide weight ratio of 1/1/0.44. After the cobalt hydroxide was completely dissolved, the pH of the solution was adjusted to 7 using ammonia. To the resulting solution, tetramine palladium nitrate was added to result in a palladium:cobalt weight ratio of 0.0015:1 in the final solution.

Impregnation/Calcination Step 1

39.6 g of impregnation solution 1 were added to 50.0 g of the 1.5 g Si/100 g Puralox SCCa 2/150 modified pre-shaped support. Aqueous slurry phase impregnation and vacuum drying were effected.

The dried impregnated support was calcined in a fluidized bed reactor by heating the material up to 300° C. at a heating rate of 2° C./min, in a 1.6% (by volume) oxygen in nitrogen flow of 2 $dm^3_n$/min. Under these conditions, the exotherm resulting from combustion of organics was roughly 40° C. As soon as the combustion started, the temperature of the gas inlet was reduced and adjusted to yield a reaction temperature of 300-310° C. The combustion phase took 3.5 hours, after which the calcination was assumed to be completed.

Impregnation/Calcination Step 2

50.0 g of the intermediate calcined material from impregnation/calcinations step 1 were subjected to the following $2^{nd}$ cobalt/platinum impregnation and calcination step:

37.04 g $Co(NO_3)_2.6H_2O$ were dissolved in 25 ml distilled water and 0.056 g of $Pt(NH_3)_4.(NO_3)_2$ (dissolved in 10 ml distilled water) were added to this solution. 50.0 g of the ex $1^{st}$ step cobalt/palladium impregnated and calcined intermediate were then added. Aqueous slurry phase impregnation and vacuum drying were effected. This vacuum dried intermediate was directly subjected to a fluidized bed calcination step, according to the following procedure using a continuous air flow of 1.6 $dm^3_n$/min, while increasing the temperature from 25° C. to 250° C. at 1° C./min and keeping it at 250° C. for 6 hours.

The catalyst precursor (i.e. after the $2^{nd}$ impregnation and calcination) was activated/reduced to obtain the catalyst by using the procedure described in Example 1, except that the end reduction temperature was 375° C.

Example 3

Preparation of Catalyst C in Accordance with the Invention

A 24 g Co/0.072 g Pt/100 g (1.5 g Si/100 g Puralox SCCa 2/150) slurry phase Fischer-Tropsch synthesis ("FTS") catalyst was prepared on a particulate modified 1.5 g Si/100 g Puralox SCCa 2/150 (trademark) pre-shaped support using two sequential aqueous slurry phase impregnation steps and drying, followed by direct fluidised bed calcination in an air/nitrogen mixture.

This preparation was done by means of two preparation steps: The first preparation step included a single impregnation step with an organic cobalt compound, while the second preparation step included a single impregnation step with an inorganic cobalt compound.

Catalyst C was prepared in exactly the same manner as Catalyst B except for the preparation of impregnation solution 1.

The preparation of impregnation solution 1 for Example 3 was done as follows:

A cobalt ammonium citrate solution containing 125 g/l cobalt was prepared by dissolving cobalt hydroxide in a citric acid solution in a water/citric acid/cobalt hydroxide weight ratio of 1/1/0.44. After the cobalt hydroxide was completely dissolved, the pH of the solution was adjusted to pH7 using ammonia. To the resulting solution, tetramine platinum nitrate was added to result in a platinum:cobalt weight ratio of 0.0015:1 in the final solution.

All of catalysts A, B, and C were tested for Fischer-Tropsch synthesis performance using a slurry phase CSTR. The following Fischer-Tropsch synthesis reaction conditions were maintained:

Reactor temperature: 230° C.
Reactor pressure: 15 bar
Catalyst inventory: ca. 10 gram
($H_2$+CO) conversion: 60%
$H_2$:CO inlet ratio: 1.6:1
Argon internal standard: 15 vol %

As all FT conditions were the same, the relative FT activity was determined by calculating the FT activity of each catalyst as mole CO converted/g catalysts/s and made relative to catalyst A.

Catalysts B and C, as prepared in accordance with the invention using cobalt citrate in the $1^{st}$ impregnation and cobalt nitrate in the $2^{nd}$ impregnation, had a relatively 15% lower cobalt loading and showed an activity enhancement of 27% and 30% respectively compared to comparative Catalyst A, which was prepared by using cobalt nitrate in both the $1^{st}$ and $2^{nd}$ impregnation step, under the reaction conditions described above.

Catalysts B and C prepared according to this invention showed a considerably higher dispersion of smaller cobalt crystallites compared to conventionally prepared cobalt nitrate-only impregnated Catalyst A. This improved dispersion is demonstrated by XRD crystallite size determination, as given in Table 1.

TABLE 1

Cobalt content, cobalt oxide crystallite size, and relative Fischer-Tropsch (FT) activity for catalysts A, B, and C

|  | Catalyst A | Catalyst B | Catalyst C |
| --- | --- | --- | --- |
| Cobalt content prior to reduction [m %] | 21 | 18 | 18 |
| XRD crystallite size of oxide precursor prior to reduction [nm] | 15 | 7 | 7 |
| Relative FT activity | 100 | 127 | 130 |

The average cobalt oxide crystallite size determined by means of XRD, for catalyst A, was 15 nm., while the average cobalt oxide crystallite size determined for catalysts B and C was significantly smaller.

Example 4

Preparation of Catalyst D in Accordance with the Invention

A 18 g Co/0.011 g Pd/0.061 g Pt/100 g (1.5 g Si/100 g Puralox SCCa 2/150) slurry phase Fischer-Tropsch synthesis ("FTS") catalyst was prepared on a particulate modified 1.5 g Si/100 g Puralox SCCa 2/150 (trademark) pre-shaped support using two sequential aqueous slurry phase preparation steps and drying, followed by direct fluidised bed calcination in a air/nitrogen mixture.

This preparation was done by means of two preparation steps: The first preparation step included a single impregnation step with an organic cobalt compound, while the second preparation step included a single impregnation step with an inorganic cobalt compound.

In particular, the catalyst was prepared as follows:
Preparation of Impregnation Solution 1

A cobalt ammonium EDTA solution containing 71.4 g/l cobalt was prepared by dissolving cobalt hydroxide in a EDTA solution in a water/EDTA/cobalt hydroxide weight ratio of 1/1/0.25. After the cobalt hydroxide was completely dissolved, the pH of the solution was adjusted to 7 using ammonia. To the resulting solution tetramine palladium nitrate was added to result in a palladium:cobalt weight ratio of 0.0015:1 in the final solution.
Impregnation/Calcination Step 1

64.6 g of impregnation solution 1 was added to 50.0 g of the 1.5 g Si/100 g Puralox SCCa 2/150 modified pre-shaped support and vacuum drying was effected.

The dried impregnated support was calcined in a fluidized bed reactor by heating the material up to 330° C. with a heating rate of 2° C./min, in a 1.6% (by volume) oxygen in nitrogen flow of 2 $dm^3_n$/min. Under these conditions, the exotherm resulting from combustion of organics is roughly 20° C. As soon as the combustion starts the temperature of the gas inlet is reduced and adjusted to yield in a reaction temperature of 300-330° C. The combustion phase took 5 hours, after which the calcination was assumed to be completed.
Impregnation/Calcination Step 2

The intermediate cobalt/palladium impregnated and calcined ex-step 1 material was subjected to the following $2^{nd}$ cobalt impregnation and calcination step:

49.5 of a solution of $Co(NO_3)_2 \cdot 6H_2O$ and $Pt(NH_3)_4 \cdot (NO_3)_2$ in water, having a cobalt content of 142.5 g/l, a Pt content of 0.21 g/ml, a density of 1.34 g/ml and a pH of 2.8 (adjusted with ammonia) was added to 35.0 g of the ex $1^{st}$ cobalt/palladium impregnated and calcined intermediate. Aqueous slurry phase impregnation and vacuum drying was effected. This vacuum dried intermediate was directly subjected to a fluidized bed calcination step, according to the following procedure using a continuous air flow of 1.6 $dm^3_n$/min, while increasing the temperature from 25° C. to 250° C. at 1° C./min and keeping it at 250° C. for 6 hours.

The catalyst precursor (i.e. after the $2^{nd}$ impregnation and calcination) was activated/reduced to obtain the catalyst by using the procedure as described in Example 1, except that the end temperature was 375° C.

Example 5

Preparation of Catalyst E in Accordance with the Invention

A 18 g Co/0.011 g Pd/0.061 g Pt/100 g (Titanium (IV) Oxide) slurry phase Fischer-Tropsch synthesis ("FTS") catalyst was prepared on a Titanium (IV) Oxide support using two sequential aqueous slurry phase preparation steps and drying, followed by direct fluidised bed calcination in a air/nitrogen mixture.

This preparation was done by means of two preparation steps: The first preparation step included a single impregnation step with an organic cobalt compound, while the second preparation step included a single impregnation step with an inorganic cobalt compound.

In particular, the catalyst was prepared as follows:
Preparation of Impregnation Solution 1

A cobalt ammonium citrate solution containing 127 g/l cobalt was prepared by dissolving cobalt hydroxide in a citric acid solution in a water/citric acid/cobalt hydroxide weight ratio of 1/1/0.44. After the cobalt hydroxide was completely dissolved, the pH of the solution was adjusted to 7 using ammonia. To the resulting solution, tetramine palladium nitrate was added to result in a palladium:cobalt weight ratio of 0.0015:1 in the final solution.
Impregnation/Calcination Step 1

39.1 g of impregnation solution 1 was added to 50.0 g of the Titanium (IV) Oxide support and vacuum drying was effected.

The dried impregnated support was calcined in a fluidized bed reactor by heating the material up to 300° C. with a heating rate of 2° C./min, in a 1.6% (by volume) oxygen in nitrogen flow of 2 $dm^3_n$/min. Under these conditions, the exotherm resulting from combustion of organics is roughly 30° C. As soon as the combustion starts the temperature of the gas inlet is reduced and adjusted to yield in a reaction temperature of 300-310° C. The combustion phase took 3.5 hours, after which the calcination was assumed to be completed.
Impregnation/Calcination Step 2

The intermediate cobalt/palladium impregnated and calcined ex-step 1 material was subjected to the following $2^{nd}$ cobalt impregnation and calcination step:

36.1 g of a solution of $Co(NO_3)_2 \cdot 6H_2O$ and $Pt(NH_3)_4 \cdot (NO_3)_2$ in water, having a cobalt content of 139.4 g/l, a Pt content of 0.21 g/ml, a density of 1.34 g/ml and a pH of 2.9 (adjusted with ammonia) was added to 25.0 g of the ex $1^{st}$ cobalt/palladium impregnated and calcined intermediate. Aqueous slurry phase impregnation and vacuum drying was effected. This vacuum dried intermediate was directly subjected to a fluidized bed calcination step, according to the following procedure using a continuous air flow of 1.6 $dm^3_n$/min, while increasing the temperature from 25° C. to 250° C. at 1° C./min and keeping it at 250° C. for 6 hours.

The catalyst precursor (i.e. after the $2^{nd}$ impregnation and calcination) was activated/reduced to obtain the catalyst by using the procedure as described in Example 1, except that the end temperature was 375° C.

Example 6

Preparation of Comparative Catalyst F

A 21 g Co/0.075 g Pt/100 g (Titanium (IV) Oxide) slurry phase Fischer-Tropsch synthesis ("FTS") catalyst was prepared on a Titanium (IV) Oxide support using two sequential aqueous slurry phase preparation steps and drying, followed by direct fluidised bed calcination in air.

This preparation was done by means of two impregnation and calcination steps, both using an inorganic cobalt compound.

In particular, the catalyst was prepared as follows:
Impregnation/Calcination Step 1

74.1 of a solution of $Co(NO_3)_2 \cdot 6H_2O$ and $Pt(NH_3)_4 \cdot (NO_3)_2$ in water, having a cobalt content of 151.5 g/l, a Pt content of 0.07 g/ml, a density of 1.37 g/ml and a pH of 2.7 (adjusted with ammonia) and 10 g water was added to 50.0 g of Titanium (IV) Oxide support and vacuum drying was effected. This vacuum dried impregnated support was directly subjected to a fluidized bed calcination step, according to the following procedure using a continuous air flow of 1.6 $dm^3_n$/min, while increasing the temperature from 25° C. to 250° C. at 1° C./min and keeping it at 250° C. for 6 hours.
Impregnation/Calcination Step 2

The intermediate cobalt/platinum impregnated and calcined ex-step 1 material was subjected to the following $2^{nd}$ cobalt impregnation and calcination step:

30 g of a solution of $Co(NO_3)_2 \cdot 6H_2O$ and $Pt(NH_3)_4 \cdot (NO_3)_2$ in water, having a cobalt content of 140.3 g/l, a Pt content of 0.21 g/ml, a density of 1.34 g/ml and a pH of 2.6 (adjusted with ammonia) was added to 30.6 g of the ex 1st cobalt/platinum impregnated and calcined intermediate. Aqueous slurry phase impregnation and vacuum drying was effected. This vacuum dried intermediate was directly subjected to a fluidized bed calcination step, according to the following procedure using a continuous air flow of 1.6 dm$^3_n$/min, while increasing the temperature from 25° C. to 250° C. at 1° C./min and keeping it at 250° C. for 6 hours.

The catalyst precursor (i.e. after the 2$^{nd}$ impregnation and calcination) was activated/reduced to obtain the catalyst by using the procedure as described in Example 1, except that the end temperature was 375° C.

Example 7

Preparation of Catalyst G in Accordance with the Invention

A 18 g Co/0.011 g Pd/0.061 g Pt/100 g (Silicon dioxide) slurry phase Fischer-Tropsch synthesis ("FTS") catalyst was prepared on a Silicon dioxide support using two sequential aqueous slurry phase preparation steps and drying, followed by direct fluidised bed calcination in a air/nitrogen mixture.

This preparation was done by means of two preparation steps: The first preparation step included a single impregnation step with an organic cobalt compound, while the second preparation step included a single impregnation step with an inorganic cobalt compound.

In particular, the catalyst was prepared as follows:
Impregnation/Calcination Step 1

39.1 g of impregnation solution 1 from Example 5 (Catalyst E) and 40 g water was added to 50.0 g of the Silicon dioxide support and vacuum drying was effected.

The dried impregnated support was calcined in a fluidized bed reactor by heating the material up to 300° C. with a heating rate of 2° C./min, in a 1.6% (by volume) oxygen in nitrogen flow of 2 dm$_n$/min. Under these conditions, the exotherm resulting from combustion of organics is roughly 30° C. As soon as the combustion starts the temperature of the gas inlet is reduced and adjusted to yield in a reaction temperature of 300-310°. The combustion phase took 3.5 hours, after which the calcination was assumed to be completed.
Impregnation/Calcination Step 2

The intermediate cobalt/palladium impregnated and calcined ex-step 1 material was subjected to the following 2$^{nd}$ cobalt impregnation and calcination step:

28.9 g of a solution of Co(NO$_3$)$_2$.6H$_2$O and Pt(NH$_3$)$_4$.(NO$_3$)$_2$ in water, having a cobalt content of 139.4 g/l, a Pt content of 0.21 g/ml, a density of 1.34 g/ml and a pH of 2.9 (adjusted with ammonia) and 10 g water was added to 20.0 g of the ex 1$^{st}$ cobalt/palladium impregnated and calcined intermediate. Aqueous slurry phase impregnation and vacuum drying was effected. This vacuum dried intermediate was directly subjected to a fluidized bed calcination step, according to the following procedure using a continuous air flow of 1.6 dm$^3_n$/min, while increasing the temperature from 25° C. to 250° C. at 1° C./min and keeping it at 250° C. for 6 hours.

The catalyst precursor (i.e. after the 2$^{nd}$ impregnation and calcination) was activated/reduced to obtain the catalyst by using the procedure as described in Example 1, except that the end temperature was 375° C.

Catalysts D, E, F and G were analysed for cobalt content and cobalt oxide crystallite size. The results are given in Table 2.

TABLE 2

Cobalt content, and cobalt oxide crystallite size, for catalysts D, E, F and G

| | Catalyst D | Catalyst E | Catalyst F | Catalyst G |
|---|---|---|---|---|
| Cobalt content prior to reduction [m %] | 18 | 18 | 21 | 18 |
| XRD crystallite size of oxide precursor prior to reduction [nm] | 8 | 10 | 32 | 8 |

Catalyst D prepared with a different organic precursor (Cobalt EDTA) in the first preparation step to that used for the preparation of Catalyst B (Cobalt citrate) also showed good dispersion of cobalt crystallites compared to the conventionally prepared cobalt nitrate-only impregnated Catalyst A.

Catalysts E and G prepared on different supports (TiO$_2$, SiO$_2$) according to this invention showed a considerably higher dispersion of smaller cobalt crystallites compared to conventionally prepared cobalt nitrate-only impregnated comparative Catalyst F. These improved dispersions are demonstrated by XRD crystallite size determination, as given in Table 2.

Example 8

Preparation of Catalyst H in Accordance with the Invention

A 23 g Co/0.00375 g Pd/0.075 g Pt/100 g (1.5 g Si/100 g Puralox SCCa 2/150) slurry phase Fischer-Tropsch synthesis ("FTS") catalyst was prepared on a particulate modified 1.5 g Si/100 g Puralox SCCa 2/150 (trademark) pre-shaped support using sequential aqueous slurry phase preparation steps and drying, followed by direct fluidised bed calcination in an air/nitrogen mixture.

This preparation was done by means of two preparation steps: The first preparation step used an organic cobalt compound, while the second preparation step used an inorganic cobalt compound. The impregnation with the inorganic cobalt compound in the second preparation step was repeated once (i.e. impregnations 2a and 2b).

In particular, the catalyst was prepared as follows:
Preparation of Impregnation Solution 1

A cobalt ammonium citrate solution containing 125 g/l cobalt was prepared by dissolving cobalt hydroxide in a citric acid solution in a water/citric acid/cobalt hydroxide weight ratio of 1/1/0.44. After the cobalt hydroxide was completely dissolved, the pH of the solution was adjusted to 7 using ammonia. To the resulting solution tetramine palladium nitrate was added to result in a palladium:cobalt weight ratio of 0.0015:1 in the final solution.
Impregnation/Calcination Step 1

13.0 g of impregnation solution 1 and 40 g of water were added to 50.0 g of the 1.5 g Si/100 g Puralox SCCa 2/150 modified pre-shaped support and vacuum drying was effected.

The dried impregnated support was calcined in a fluidized bed reactor by heating the material up to 300° C. with a heating rate of 2° C./min, in a 1.6% (by volume) oxygen in nitrogen flow of 2 dm$^3_n$/min. Under these conditions, the exotherm resulting from combustion of organics is roughly 30° C. As soon as the combustion starts the temperature of the gas inlet is reduced and adjusted to yield in a reaction temperature of 300-310° C. The combustion phase took 2 hours, after which the calcination was assumed to be completed.

Impregnation/Calcination Step 2a

The intermediate cobalt/palladium impregnated and calcined ex-step 1 material was subjected to the following $2^{nd}$ cobalt impregnation and calcination step:

59.4 g of a solution of $Co(NO_3)_2 \cdot 6H_2O$ and $Pt(NH_3)_4 \cdot (NO_3)_2$ in water, having a cobalt content of 151 g/l, a Pt content of 0.21 g/ml, a density of 1.37 g/ml and a pH of 2.7 (adjusted with ammonia) was added to 40.0 g of the ex $1^{st}$ cobalt/palladium impregnated and calcined intermediate. Aqueous slurry phase impregnation and vacuum drying was effected. This vacuum dried intermediate was directly subjected to a fluidized bed calcination step, according to the following procedure using a continuous air flow of 1.6 $dm^3{}_n$/min, while increasing the temperature from 25° C. to 250° C. at 1° C./min and keeping it at 250° C. for 6 hours.

Impregnation/Calcination Step 2b

The intermediate ex-step 2a cobalt/palladium/platinum impregnated and calcined material was subjected to the following cobalt impregnation and calcination step:

40.9 g of a solution of $Co(NO_3)_2 \cdot 6H_2O$ and $Pt(NH_3)_4 \cdot (NO_3)_2$ in water, having a cobalt content of 139 g/l, a Pt content of 0.53 g/ml, a density of 1.34 g/ml and a pH of 2.9 (adjusted with ammonia) was added to 40.0 g of the ex-step 2a cobalt/palladium/platinum impregnated and calcined intermediate. Aqueous slurry phase impregnation and vacuum drying was effected. This vacuum dried intermediate was directly subjected to a fluidized bed calcination step, according to the following procedure using a continuous air flow of 1.6 $dm^3{}_n$/min, while increasing the temperature from 25° C. to 250° C. at 1° C./min and keeping it at 250° C. for 6 hours.

The catalyst precursor (i.e. after last impregnation and calcination) was activated/reduced to obtain the catalyst by using the procedure as described in Example 1, except that the end temperature was 375° C.

Example 9

Preparation of Catalyst I in Accordance with the Invention

A 18 g Co/0.011 g Pd/0.023 g Pt/100 g (1.5 g Si/100 g Puralox SCCa 2/150) slurry phase Fischer-Tropsch synthesis ("FTS") catalyst was prepared on a particulate modified 1.5 g Si/100 g Puralox SCCa 2/150 (trademark) pre-shaped support using three sequential aqueous slurry phase preparation steps and drying, followed by direct fluidised bed calcination in a air/nitrogen mixture.

This preparation was done by means of two preparation steps: The first preparation step used an organic cobalt compound, while the second preparation step an inorganic cobalt compound. The impregnation with the organic cobalt compound in the first preparation step was repeated once (i.e. impregnations 1a and 1b).

In particular, the catalyst was prepared as follows:

Preparation of Impregnation Solution 1

A cobalt ammonium citrate solution containing 125 g/l cobalt was prepared by dissolving cobalt hydroxide in a citric acid solution in a water/citric acid/cobalt hydroxide weight ratio of 1/1/0.44. After the cobalt hydroxide was completely dissolved, the pH of the solution was adjusted to 7 using ammonia. To the resulting solution tetramine palladium nitrate was added to result in a palladium:cobalt weight ratio of 0.0015:1 in the final solution.

Impregnation/Calcination Step 1a 13.0 g of impregnation solution 1 and 40 g of water was added to 50.0 g of the 1.5 g Si/100 g Puralox SCCa 2/150 modified pre-shaped support and vacuum drying was effected.

The dried impregnated support was calcined in a fluidized bed reactor by heating the material up to 300° C. with a heating rate of 2° C./min, in a 1.6% (by volume) oxygen in nitrogen flow of 2 $dm^3{}_n$/min. Under these conditions, the exotherm resulting from combustion of organics is roughly 30° C. As soon as the combustion starts the temperature of the gas inlet is reduced and adjusted to yield in a reaction temperature of 300-310° C. The combustion phase took 2 hours, after which the calcination was assumed to be completed.

Impregnation/Calcination Step 1b 20.8 g of impregnation solution 1 was added to 40.0 g of the ex-step 1a cobalt/palladium impregnated and calcined intermediate and vacuum drying was effected.

The dried impregnated support was calcined in a fluidized bed reactor by heating the material up to 300° C. with a heating rate of 2° C./min, in a 1.6% (by volume) oxygen in nitrogen flow of 2 $dm^3{}_n$/min. Under these conditions, the exotherm resulting from combustion of organics is roughly 30° C. As soon as the combustion starts the temperature of the gas inlet is reduced and adjusted to yield in a reaction temperature of 300-310° C. The combustion phase took 3.5 hours, after which the calcination was assumed to be completed.

Impregnation/Calcination Step 2

The intermediate ex-step 1b cobalt/palladium impregnated and calcined material was subjected to the following $3^{rd}$ cobalt impregnation and calcination step:

42.4 g of a solution of $Co(NO_3)_2 \cdot 6H_2O$ and $P(NH_3)_4 \cdot (NO_3)_2$ in water, having a cobalt content of 143 g/l, a Pt content of 0.54 g/ml, a density of 1.34 g/ml and a pH of 2.8 (adjusted with ammonia) was added to 30.0 g of the ex-step 1b cobalt/palladium impregnated and calcined intermediate.

Aqueous slurry phase impregnation and vacuum drying was effected. This vacuum dried intermediate was directly subjected to a fluidized bed calcination step, according to the following procedure using a continuous air flow of 1.6 $dm^3{}_n$/min, while increasing the temperature from 25° C. to 250° C. at 1° C./min and keeping it at 250° C. for 6 hours.

The catalyst precursor (i.e. after the last impregnation and calcination) was activated/reduced to obtain the catalyst by using the procedure as described in Example 1, except that the end temperature was 375° C.

Catalysts H and I were tested for Fischer-Tropsch synthesis performance on exactly the same basis as for Catalysts A, B and C hereinbefore described. The results are given in Table 3.

TABLE 3

Cobalt content, cobalt oxide crystallite size, and relative Fischer-Tropsch (FT) activity for catalysts A, H, and I

|  | Catalyst H | Catalyst I | Catalyst A |
| --- | --- | --- | --- |
| Cobalt content prior to reduction [m %] | 23 | 18 | 21 |
| XRD crystallite size of oxide precursor prior to reduction [nm] | 12 | 7 | 15 |
| Relative FT activity | 143 | 138 | 100 |

It was thus surprisingly found that when, during the first preparation step, an organic cobalt compound/complex is used followed by impregnation, in a second preparation step, with a cobalt salt, a catalyst having an increased Fischer- Tropsch activity is obtained. This is most likely due to the high cobalt (metal and/or oxide) dispersion and, at the same time, a desired high cobalt loading.

The invention thus overcomes problems associated with known processes for preparing Fischer-Tropsch catalysts whereby, on the one hand, high dispersions of cobalt on the catalyst support can be achieved when using low metal loading, while on the other hand, for many Fischer-Tropsch synthesis reactions, low cobalt loadings do not provide a desired high activity. Hitherto, when it has then been attempted to increase the cobalt loading, metal dispersion often decreased to unacceptable levels. It was thus surprisingly found that this problem was avoided with the process of the present invention.

Example 10

Preparation of Catalyst J in Accordance with the Invention

A 26 g Co/0.075 Pt/100 g (1.5 g Si/100 g Puralox SCCa 2/150) slurry phase Fischer-Tropsch synthesis ("FTS") catalyst was prepared on a particulate modified 1.5 g Si/100 g Puralox SCCa 2/150 (trademark) pre-shaped support using two sequential slurry phase preparation steps and drying, followed by direct fluidised bed calcination in air.

This preparation was done by means of two preparation steps: The first preparation step included a single impregnation step with an organic cobalt compound and an organic solvent, while the second preparation step included a single impregnation step with an inorganic cobalt compound and water as a solvent.

In particular, the catalyst was prepared as follows:

Impregnation/Calcination Step 1

43 g of Co(acac)$_2$ (i.e. cobalt acetylacetonate; Co(C$_5$H$_7$O$_2$)$_2$) and 0.049 g Pt(NH$_3$)$_4$.(NO$_3$)$_2$ were dissolved in 120 ml of Toluene. 100 grams of 1.5 g Si/100 g Puralox SCCa 2/150 modified pre-shaped support was then added to this solution. Organic slurry phase impregnation and vacuum drying were effected.

This vacuum dried intermediate was directly subjected to a fluidized bed calcination step using a continuous air flow of 1.7 dm$^3_n$/min, while increasing the temperature from 25° C. to 250° C. at 1° C./min and keeping it at 250° C. for 6 hours.

Impregnation/Calcination Step 2

100 g of this intermediate calcined material were subjected to the following 2nd cobalt/platinum impregnation and calcination step: 69.5 g Co(NO$_3$)$_2$.6H$_2$O were dissolved in 100 ml distilled water and 0.087 g of Pt(NH$_3$)$_4$.(NO$_3$)$_2$ (dissolved in 10 ml distilled water) were added to this solution, and 100 g of the ex 1$^{st}$ cobalt/platinum impregnated and calcined intermediate were added. Aqueous slurry phase impregnation and vacuum drying were effected. This vacuum dried intermediate was directly subjected to a fluidized bed calcination step, according to the following procedure using a continuous air flow of 1.7 dm$^3_n$/min, while increasing the temperature from 25° C. to 250° C. at 1° C./min and keeping it at 250° C. for 6 hours.

The catalyst precursor (i.e. after the 2$^{nd}$ impregnation and calcination) was activated/reduced to obtain the catalyst by using the same procedure as described in Example 1.

TABLE 4

Cobalt content and cobalt oxide crystallite size for catalysts A, B, C and J

| | Catalyst A | Catalyst B | Catalyst C | Catalysts J |
|---|---|---|---|---|
| Cobalt content prior to reduction [m %] | 21 | 18 | 18 | 18 |
| XRD crystallite size of oxide precursor prior to reduction [nm] | 15 | 7 | 7 | 9 |

Example 11

Fatty Acid Hydrogenation

The hydrogenating performance of (Catalyst B) was determined by the hydrogenation of 150 g of tallow fatty acid (iodine value 50.6). Catalyst runs were conducted in a 300 ml autoclave using ~830 mg of prereduced cobalt catalyst such that the cobalt content in the reactor was 0.1 weight percent. Reactions were run at a hydrogen pressure of 20 bar, a temperature of 200° C. and a stirring speed of 1600 rpm.

The hydrogen consumption was monitored for 4 hours. In addition, the end iodine value was measured by the Wijs method as described in A.O.C.S. Official Method Cd 1-25 (1990).

The catalyst afforded a 56% conversion of the fatty acid sample after 4 hour. This resulted in an end iodine value of 22.5.

The results are set out in Table 5

TABLE 5

| Time (min) | H$_2$ consumption (I) | Conversion (%) | Iodine value |
|---|---|---|---|
| 0 | 0.0 | 0 | 50.9 |
| 20 | 0.93 | 14 | 44 |
| 40 | 1.55 | 23 | 39.3 |
| 80 | 2.50 | 36 | 32.3 |
| 160 | 3.42 | 50 | 25.5 |
| 240 | 3.81 | 56 | 22.5 |

The invention claimed is:

1. A process for preparing a catalyst precursor, which process includes
   in a first preparation step, impregnating a particulate catalyst support with an organic cobalt or nickel compound in a carrier liquid, to form an impregnated intermediate and calcining the impregnated intermediate at a calcination temperature which is not above 400° C., to obtain a calcined intermediate; and
   thereafter, in a second preparation step, impregnating the calcined intermediate from the first preparation step, with an inorganic cobalt or nickel salt in a carrier liquid, to obtain an impregnated support, and calcining the impregnated support, to obtain the catalyst precursor, wherein none of the inorganic cobalt or nickel salt used in the second preparation step is present during the first preparation step.

2. A process according to claim 1, wherein none of the organic cobalt or nickel compound of the first preparation step is present during the second preparation step.

3. A process according to claim 1, wherein the impregnated intermediate of the first preparation step is at least partially dried prior to the calcination thereof, and/or wherein the impregnated support of the second preparation step is at least partially dried prior to the calcination thereof.

4. A process according to claim 3, which includes, in the first preparation step, repeating, at least once, the impregnation with the organic cobalt or nickel compound, the at least partial drying of the impregnated intermediate, and the calcination of the at least partially dried impregnated intermediate, to obtain a higher cobalt or nickel loading in the calcined intermediate.

5. A process according to claim 3, which includes, in the second preparation step, repeating, at least once, the impregnation with the inorganic cobalt or nickel salt, the at least partial drying of the impregnated support, and the calcination of the partially dried impregnated support, to obtain a higher cobalt or nickel loading in the catalyst precursor.

6. A process according to claim 1, wherein an organic cobalt compound and an inorganic cobalt salt are used.

7. A process according to claim 6, wherein the inorganic cobalt salt of the second preparation step is $Co(NO_3)_2 \cdot 6H_2O$, with the $Co(NO_3)_2 \cdot 6H_2O$ being dissolved in water as the carrier liquid.

8. A process according to claim 6, wherein the organic cobalt compound of the first preparation step is that obtained by reacting a cobalt compound with an organic acid, optionally in the presence of a counterion source.

9. A process according to claim 8 wherein, in respect of the organic cobalt compound of the first preparation step, the organic acid is selected from citric acid ($C_6H_8O_7$), succinic acid ($C_4H_6O_4$), oxalic acid ($C_2H_2O_4$), acetic acid ($C_2H_4O_2$), gluconic acid ($C_6H_{12}O_7$) and EDTA; the cobalt compound is cobalt hydroxide; and the counterion source, when present, is ammonia.

10. A process according to claim 6, wherein the organic cobalt compound of the first preparation step is that obtained by reaction of a cobalt compound with acetylacetone ($C_5H_8O_2$).

11. A process according to claim 6, wherein the organic cobalt compound of the first preparation step is cobalt ammonium citrate.

12. A process according to claim 6, wherein the organic cobalt compound is dissolved in water as the carrier liquid.

13. A process according to claim 6, wherein the impregnation and drying during the first and the second preparation steps are carried out at above 25° C. and at sub-atmospheric pressure, thereby providing conditions at which the inorganic cobalt salt and the organic cobalt compound will not readily decompose.

14. A process according to claim 6, wherein the catalyst precursor is a cobalt-based Fischer-Tropsch synthesis catalyst precursor.

15. A process according to claim 6, wherein the catalyst precursor is a cobalt-based hydrogenation catalyst precursor.

16. A process for preparing a catalyst, which includes
in a first preparation step, impregnating a particulate catalyst support with an organic cobalt or nickel compound in a carrier liquid, to form an impregnated intermediate and calcining the impregnated intermediate at a calcination temperature which is not above 400° C., to obtain a calcined intermediate;
thereafter, in a second preparation step, impregnating the calcined intermediate from the first preparation step, with an inorganic cobalt or nickel salt in a carrier liquid, to obtain an impregnated support, and calcining the impregnated support, to obtain a catalyst precursor, wherein none of the inorganic cobalt or nickel salt used in the second preparation step is present during the first preparation step; and
reducing the catalyst precursor, thereby to obtain the catalyst.

17. A hydrocarbon synthesis process which comprises
preparing a catalyst by
in a first preparation step, impregnating a particulate catalyst support with an organic cobalt or nickel compound in a carrier liquid, to form an impregnated intermediate and calcining the impregnated intermediate at a calcination temperature which is not above 400° C., to obtain a calcined intermediate;
thereafter, in a second preparation step, impregnating the calcined intermediate from the first preparation step, with an inorganic cobalt or nickel salt in a carrier liquid, to obtain an impregnated support, and calcining the impregnated support, to obtain a catalyst precursor, with none of the inorganic cobalt or nickel salt used in the second preparation step being present during the first preparation step; and
reducing the catalyst precursor, thereby to obtain the catalyst; and
contacting hydrogen with carbon monoxide at a temperature above 100° C. and a pressure of at least 10 bar with the catalyst, to produce hydrocarbons and, optionally, oxygenates of hydrocarbons.

18. A process according to claim 17 which is a slurry bed Fischer-Tropsch process for producing a wax product.

19. A process according to claim 17 which includes a hydroprocessing step for converting the hydrocarbons and, optionally, oxygenates to liquid fuels and/or chemicals.

20. A hydrogenation process which comprises
preparing a catalyst by
in a first preparation step, impregnating a particulate catalyst support with an organic cobalt or nickel compound in a carrier liquid, to form an impregnated intermediate and calcining the impregnated intermediate at a calcination temperature which is not above 400° C., to obtain a calcined intermediate; and
thereafter, in a second preparation step, impregnating the calcined intermediate from the first preparation step, with an inorganic cobalt or nickel salt in a carrier liquid, to obtain an impregnated support, and calcining the impregnated support, to obtain a catalyst precursor, with none of the inorganic cobalt or nickel salt used in the second preparation step being present during the first preparation step; and
reducing the catalyst precursor, thereby to obtain the catalyst; and
contacting hydrogen and an organic compound with the catalyst, to hydrogenate the organic compound.

* * * * *